(12) United States Patent
Grüner

(10) Patent No.: US 12,714,526 B2
(45) Date of Patent: Aug. 25, 2026

(54) STEERING GEAR FOR A SURGICAL INSTRUMENT AND SURGICAL INSTRUMENT EQUIPPED THEREWITH

(71) Applicant: KARL STORZ SE & CO. KG, Tuttlingen (DE)

(72) Inventor: Sven Axel Grüner, Tuttlingen (DE)

(73) Assignee: KARL STORZ S.E. & Co. KG, Tuttlingen (DE)

(*) Notice: Subject to any disclaimer, the term of this patent is extended or adjusted under 35 U.S.C. 154(b) by 285 days.

(21) Appl. No.: 18/536,704

(22) Filed: Dec. 12, 2023

(65) Prior Publication Data

US 2024/0197425 A1 Jun. 20, 2024

(30) Foreign Application Priority Data

Dec. 20, 2022 (DE) ......................... 102022134210.7

(51) Int. Cl.
*A61B 34/00* (2016.01)
*A61B 34/30* (2016.01)

(52) U.S. Cl.
CPC ........ *A61B 34/71* (2016.02); *A61B 2034/301* (2016.02)

(58) Field of Classification Search
CPC .............. A61B 34/71; A61B 2034/301; A61B 2017/003; A61B 2017/00323; A61B 2017/00327; A61B 17/29
See application file for complete search history.

(56) References Cited

U.S. PATENT DOCUMENTS 10,105,128 B2 10/2018 Cooper et al.
2021/0038331 A1* 2/2021 Grüner .................. B25J 9/1035
2021/0381585 A1* 12/2021 Crawford ............... F16H 37/16

FOREIGN PATENT DOCUMENTS

DE 102019121092 A1 2/2021
WO 2020218920 A2 10/2020
WO 2023006684 A1 2/2023
WO 2023006685 A1 2/2023

* cited by examiner

*Primary Examiner* — Niketa Patel
*Assistant Examiner* — Sebastian X Lukjan
(74) *Attorney, Agent, or Firm* — Brooks Kushman, P.C.

(57) ABSTRACT

The present disclosure provides a steering gear for a surgical instrument and the surgical instrument. The steering gear includes two drives for the spatial alignment of a wobble plate rotatively coupled to a main shaft rotatable about a gimbal. The steering gear includes two linear slides each displaceably arranged along a guide axis connected to the two drives. Each linear slide is operatively connected to the wobble plate by an engagement element pair having an engagement opening and a lever element having a rod portion, and a head portion. One of the engagement elements is present on a circumference of the wobble plate and the other engagement element of the engagement element pair is present on a surface portion of the respective linear slide facing the wobble plate, said surface portion being a surface portion on a longitudinal side of the linear slide parallel to the guide axis.

11 Claims, 6 Drawing Sheets

STEERING GEAR FOR A SURGICAL INSTRUMENT AND SURGICAL INSTRUMENT EQUIPPED THEREWITH

CROSS-REFERENCE TO RELATED APPLICATIONS

This application claims priority of German Patent Application No. 10 2022 134 210.7 filed on Dec. 20, 2023, the contents of which are incorporated herein.

TECHNICAL FIELD

The disclosure relates to a steering gear of a surgical instrument and to a surgical instrument comprising such a steering gear.

BACKGROUND

The prior art has disclosed surgical instruments that can be guided manually by means of a handle or by a robot and that have a tool at the distal end of an elongate shaft, it being possible to pivot said tool vis-à-vis the shaft, which defines a main axis, by way of an angling mechanism made of a plurality of meshing pivot members. These pivot members are connected by way of a multiplicity of steering wires or steering cables in order to attain delicate tool tip control. For actuation purposes, the steering wires may be fastened to a gimbal-mounted wobble plate which can be aligned in space by a steering gear.

U.S. Pat. No. 10,105,128 B2 has disclosed the practice of using two parallel rods to actuate a gimbal-mounted wobble plate, which is connected to an angling mechanism by way of steering wires. To this end, the rods have a ball socket at one end for accommodating a spherical element coupled to the wobble plate. At their other end, these spherical joint rods are connected via rotary joints to a respective gear wheel quadrant that is actuated by a drive gear wheel, in order to move the spherical joint rods backward and forward linearly for the purpose of aligning the wobble plate. However, the wobble plate control with spherical joint rods is not particularly direct, but afflicted by play and has a disadvantageous power flow. Moreover, a rotation of the wobble plate about the shaft axis is not possible in this case.

In this respect, DE 10 2019 121 092 A1 proposes a surgical instrument which uses a differential gear with two opposing input bevel gears and an output bevel gear which meshes with the input bevel gears and is coupled to the wobble plate. In this way, the adjustment angles of two drives are transmitted directly to the wobble plate in order to appropriately align or angle the tool tip. Further, the wobble plate there is gimbal-mounted on a rotatable main shaft by means of a universal joint plate and can therefore be rotated with the main shaft about the shaft axis. However, the coaxial arrangement of the two drives opposite one another in a plane and orthogonal to the main axis requires an increased amount of installation space.

SUMMARY

Proceeding from this prior art, it is an object of the present disclosure to provide an improved steering gear for a surgical instrument for the spatial alignment of a wobble plate.

This object is achieved by a steering gear having the features of claim 1.

The further object of providing a surgical instrument with an improved steering gear is achieved by the surgical instrument having the features of independent claim 11.

Developments or preferred embodiments are explained in the dependent claims.

According to a first embodiment, the steering gear according to the disclosure, which is provided and designed for a surgical instrument, comprises at least two drives for the spatial alignment of a wobble plate. The wobble plate is rotatively coupled to a main shaft which defines a main axis A, about which the main shaft is rotatable. On account of the coupling, the wobble plate is able to rotate together with the main shaft. Further, the wobble plate is gimbal-mounted about a center located on the main axis A. According to the disclosure, the steering gear comprises at least two linear slides, which are each displaceably arranged along a guide axis $B_x$ parallel to the main axis A and connected to the at least two drives. Each linear slide is operatively connected to the wobble plate by way of an engagement element pair. The engagement elements of the pair are formed by an engagement opening and a lever element. At a free end of a rod portion, the lever element comprises a head portion for movable accommodation in the engagement opening. In this case, one of the engagement elements of the engagement element pair is present on a circumference of the wobble plate and the other engagement element of the engagement element pair is present on a surface portion of the respective linear slide facing the wobble plate, said surface portion being a surface portion on a longitudinal side of the linear slide parallel to the guide axis $B_x$. In this way, the head portion of each lever element is located on a circumferential line around the wobble plate center since the operative connection of the wobble plate to the at least two linear slides consequently has at least two lever elements, with the result that a pivot plane of the wobble plate is defined by the head portions of the lever elements and the center of the wobble plate.

Using the steering gear according to the disclosure, it is possible to pivot the wobble plate directly by linear drives in two spatial directions for the purpose of actuating a distal angling mechanism, with the wobble plate additionally being able to rotate together with the main shaft. This ensures that the steering wires fastened to the wobble plate are co-rotated when the main shaft is rotated and cannot wrap around the main shaft. In this case, the wobble plate can rotate with the main shaft both when said wobble plate is in the neutral position, which is to say in the non-articulated state when the pivot plane of the wobble plate is orthogonal to the main axis A, and following an articulation into the pivoted position, in which the main axis A intersects the pivot plane of the wobble plate at an angle that deviates from 90°. To pivot the wobble plate from the neutral position, at least one of the linear slides is moved along the guide axis $B_x$ parallel to the main axis A, wherein the lever element, as rod-shaped force transmission element of the respective engagement element pair, follows the movement of the linear slide. With this movement there is a change in the pose of the head portion of the lever element and hence in the pose of the pivot plane, with the result that the wobble plate is accordingly deflected vis-à-vis the main axis A about its center. The center of the wobble plate, about which the wobble plate can also rotate as a result of the coupling to the main shaft, is defined by the point of intersection of the axes of rotation arising from the gimbal mount.

Within the meaning of the disclosure, a “gimbal mount” is presently understood to be any mount of the wobble plate which allows pivoting of the wobble plate, which is rotatively coupled to the main shaft, in two directions orthogonal to the main axis (tilting and yawing). This comprises both conventional mounting variants with two orthogonal axis pairs and mounting variants with a deviating number and alignment of axis elements, provided these precisely permit movements of the wobble plate in two spatial directions orthogonal to the main axis A.

The index x in the label of the guide axis $B_x$ represents a natural number (1, 2, 3, or 4) and is used presently for simplified labeling of the guide axes $B_x$, which are each assigned to a linear slide. By way of index 1, the guide axis $B_1$ is assigned to a first linear slide. A guide axis $B_2$ is assigned to a second linear slide, etc.

According to a further embodiment of the steering gear according to the disclosure, the head portion is a spherical head portion having a spherical shape at least in part or a T-head portion shaped cylindrically at least in part. In the embodiment of the lever element with the T-head portion, provision can be made for the lever element to be rotatably mounted about the longitudinal axis of the rod portion or for the T-head portion to be rotatably mounted on the rod portion, in order to be able to follow the movement of the linear slides engaging with the wobble plate. A "T-head portion" is understood to mean that the T-head portion shaped like a cylinder runs orthogonal to the rod portion and is arranged centrally on the rod portion, with the result that the rod portion and the head portion have a T-shape in side view.

According to a further embodiment of the steering gear according to the disclosure, provision is made for the wobble plate to comprise the engagement opening and for each linear slide to comprise a respective one of the lever elements. To this end, the engagement opening is designed either as a circumferential groove running all along the circumferential edge of the wobble plate or as a circumferential recess running all along the circumferential edge of the wobble plate. Then, the lever element is arranged on the surface portion of the respective linear slide facing the wobble plate, with the result that the rod portion points in the radial direction toward the main axis A and the head portion of each lever element is movably accommodated in the circumferential groove or in the circumferential recess.

With the circumferential groove or the circumferential recess as common engagement opening for each lever element, it is possible to dispense with complicated spherical joint rods within the scope of compensating lateral displacements. In contrast to the circumferential groove, which is bounded on both sides, the circumferential recess is bounded on only one side, wherein the width of the groove or recess is dimensioned in accordance with the guided accommodation/abutment of the head portion of the lever elements. The centers of the head portions of the lever elements, the rod portions or longitudinal axes of which point in the radial direction toward the main axis A, are always exactly in the pivot plane of the wobble disk as a result of the guidance in the circumferential groove or on the circumferential recess. If the linear slides are moved, these centers of the head portions are displaced with the lever elements and thus lead to the wobble plate pivoting. Coupling of the wobble plate with the main shaft for joint rotation about the main shaft is possible without problems since the circumferential groove or the circumferential recess is present all round.

To allow an extensive force transmission when using lever elements with a spherical head portion in this case, the engagement element pair according to one development of the steering gear according to the disclosure may comprise a slide block element for each lever element formed with a spherical head portion. This slide block element is designed to be accommodated in the all-round circumferential groove or in the all-round circumferential recess and comprises a ball socket, in which the spherical head portion of the lever element can be movably accommodated. Optionally, slide block elements, which are assigned to the lever elements of adjacent linear slides and therefore arranged adjacently in the circumferential groove or on the circumferential recess, can be interconnected by way of an elastic connection element in each case and may jointly form a clamp element.

In a manner analogous to the extent of the circumferential groove/circumferential recess, such a slide block element may have an arcuate design, wherein the ball socket for articulated accommodation of the spherical head portion is by preference placed centrally in the slide block element. Lever elements comprising a T-head portion can also dispense with such a slide block element since, in contrast with a spherical head portion whose force transmission is punctiform, the T-head portions can transmit force through linear contact.

According to a further embodiment of the steering gear according to the disclosure, in which the wobble plate is designed with the all-round circumferential groove as engagement opening, the steering gear may comprise two linear slides, on each of which a lever element is arranged. In this case, the arrangement of the lever elements on the linear slides and the arrangement of the two linear slides in relation to the wobble plate are matched to one another in such a way that two differently oriented pivot axes $C_1$, $C_2$ are defined by each of the two head portions of the two lever elements together with the center of the wobble plate. That is to say, an angle of neither 0° nor 180° is spanned between the two pivot axes $C_1$, $C_2$. In a preferred embodiment, the two pivot axes $C_1$, $C_2$ run orthogonal to one another when the wobble plate is in the neutral position, in which the wobble plate, in the non-deflected state, is orthogonal to the main axis A.

According to an alternative embodiment of the steering gear according to the disclosure, in which the wobble plate is designed with the all-round circumferential recess as engagement opening, the steering gear comprises three linear slides, each with a lever element, and three drives connected to the linear slides. In this case, the arrangement of the lever elements on the linear slides and the arrangement of the three linear slides in relation to the wobble plate are matched to one another in such a way that three differently oriented pivot axes $C_1$, $C_2$, $C_3$ are defined by each of the three head portions of the three lever elements together with the center of the wobble plate. In a preferred embodiment, the three head portions of the three lever elements are arranged at the same distance from the center of the wobble plate where possible and are arranged spaced apart from one another as uniformly as possible, with the result that the three pivot axes $C_1$, $C_2$, $C_3$ in each case have an angle of approximately 120°±10° from one another and yield 360° in total when the wobble plate is in the neutral position.

In this embodiment, the head portions of the three lever elements are located in the corners of an equilateral triangle, wherein the pivot axes $C_1$, $C_2$, $C_3$ correspond to the perpendicular bisectors of the equilateral triangle. In this case, the center of the wobble plate, about which the wobble plate is pivoted, corresponds to the point of intersection of the perpendicular bisectors in this equilateral triangle. Since the pivot plane is already defined by way of the three head portions in this embodiment, this arrangement embodies the gimbal mount of the wobble plate at the same time, with the result that additional elements for a gimbal mount of the wobble plate can be dispensed with here. However, alternative embodiments of this preferred arrangement are also conceivable, for example if the installation space design does not allow for a uniformly distributed arrangement of the three head portions. In alternative, likewise functional arrangements, the head portions of the lever elements may therefore also be located in the corners of any isosceles or irregular triangle, with the point of intersection of the perpendicular bisectors of the triangle corresponding to the center of the wobble plate.

Consequently, a right angle or an acute angle may also be present between two of the three pivot axes, with the result that at least one or each of the two pivot axes spans an obtuse angle with the third pivot axis. For example, if there is a right angle or an acute angle ranging from 10° to 90° between two of the pivot axes, then there is, in the case of an isosceles arrangement of the head portions, an obtuse angle ranging from 135° to 175° between each of the two pivot axes and the third pivot axis, with the result that the angles total 360°. The angle measures should be understood to be merely exemplary and are not intended to limit the scope of protection. A minimum acute angle between two of the three pivot axes arises if two of the three head portions are arranged next to one another on the circumferential recess, and accordingly depends on the diameter of the head portions and their distance from the center of the wobble plate. In principle, it is also conceivable that two of the three pivot axes span a reflex angle (>180°), with the result that at least one of these two pivot axes spans an acute angle with the third pivot axis.

According to yet a further alternative embodiment of the steering gear according to the disclosure, wherein the wobble plate is likewise designed with the all-round circumferential recess as engagement opening, the steering gear comprises four linear slides, each with a lever element. In this case, the arrangement of the lever elements on the linear slides and the arrangement of the four linear slides in relation to the wobble plate are matched to one another in such a way that in each case two of the lever elements are arranged opposite one another. Then, two pivot axes $C_1$, $C_2$, which are defined by the head portions of opposing lever elements together with the center of the wobble plate, run orthogonal to one another. In this case, two drives are connected in pairwise fashion with the linear drives of opposing lever elements. This suffices since, for the purpose of aligning the wobble plate, the linear slides of opposing lever elements are controlled exactly oppositely by the same drive via a reversing gear. However, if there is sufficient installation space, it is alternatively also possible, in principle, to use an independent drive for each of the four linear slides.

According to yet a further alternative embodiment of the steering gear according to the disclosure, provision is made for at least two of the lever elements to be arranged on the wobble plate, wherein the associated engagement openings are present in at least two linear slides. The lever elements, which are formed with the spherical head portion, extend from the circumferential edge of the wobble plate in the radial direction. And of the at least two linear slides, a first linear slide comprises, as engagement opening, an arcuate groove running around the main axis A in the surface portion facing the wobble plate. The spherical head portion of a first of the lever elements is movably accommodated in the arcuate groove of the first linear slide. A second linear slide comprises, as engagement opening, a cylindrical drilled hole which is formed in the surface portion facing the wobble plate and in which the spherical head portion of a second of the lever elements is movably accommodated. The axis of the cylindrical drilled hole in the second linear slide in this case intersects the main axis A orthogonally. The spherical head portion of the second lever element can move linearly in this drilled hole and can compensate the distance between lever element and linear slide which varies when the wobble plate is pivoted. In this case, the arrangement of the engagement openings in the linear slides and the arrangement of the at least two linear slides in relation to the wobble plate are matched to the arrangement of the at least two lever elements on the wobble plate. In this case, the latter has a central portion which is rotatively coupled to the main shaft and rotatably mounted in a steering ring of the wobble plate, said steering ring having the circumferential edge on which the at least two lever arms are arranged.

In this way, the central portion of the wobble plate, to which the steering wires are fastened, can be rotated with the main shaft while the spatial alignment of the wobble plate is brought about by way of the steering ring, which is not rotatable as a consequence of the engagement of the lever elements with the linear slides. This is due to the engagement of the spherical head portion of the second lever element in the cylindrical drilled hole of the second linear slide, while the head portion of the first lever element is guided in the arcuate groove in the first linear slide. An arcuate groove is understood to mean a groove, bounded on both sides, in the shape of a circular arc, the circle center of which is located on the main axis A. Hence, the arcuate groove runs virtually parallel to the circumferential edge of the wobble plate when the latter is in the neutral position orthogonal to the main axis A.

For example, the steering gear of this embodiment may comprise precisely two lever elements on the circumferential edge of the wobble plate, the lever elements engaging with the first and second linear slide. In this case, the first and the second lever element, whose spherical head portions together with the center of the wobble plate define two pivot axes $C_1$, $C_2$, are arranged on the circumferential edge of the wobble plate in such a way that the two pivot axes $C_1$, $C_2$ are oriented differently, which is to say span an angle of neither 0° nor 180°. It is advantageous if the angle between the two pivot axes $C_1$, $C_2$ is in a range from 60° to 120°. An orthogonal arrangement of the two lever elements on the circumferential edge of the wobble plate is particularly preferred, which is to say that the longitudinal axes of the rod portions of the first and second lever element, corresponding here to the pivot axes $C_1$, $C_2$, run orthogonal to one another. Accordingly, the linear slides with the engagement openings are suitably arranged for engagement with the lever elements.

Further, according to a further embodiment, a steering gear according to the disclosure can comprise at least one housing component which provides a linear guide for each linear slide. For example, the linear guide may consist of a guide groove parallel to the guide axis $B_x$ being formed in the housing component for each linear slide. Accordingly, each linear slide comprises at least one guide element on a second longitudinal side, which is parallel to the guide axis $B_x$ and which differs from the longitudinal side with the surface portion facing the wobble plate, the guide element being accommodated in longitudinally movable fashion in the respective guide groove. The second longitudinal side of the linear slide, on which the guide element is formed, can—depending on the design of the housing component—be facing away from or adjacent to the longitudinal side of the linear slide with the surface portion facing the wobble plate. Alternatively, for the purpose of longitudinally guiding the linear guides, a guide element for each linear guide may conversely be formed parallel to the guide axis $B_x$ in the housing component, and each linear slide may have a guide groove displaceably accommodating the guide element on a second longitudinal side of the linear guide which differs from the longitudinal side with the surface portion facing the wobble plate.

According to a further embodiment of the steering gear according to the disclosure, the surface portion facing the wobble plate is concavely shaped, wherein the concave surface portion preferably corresponds to a lateral cylindrical surface portion around the main axis A.

Finally, a development of the steering gear according to the disclosure provides for the drive, to which the linear slide is connected, to be a linear motor or a rotary motor connected to the linear slide via a spindle, or a hydraulic or pneumatic cylinder.

According to a first embodiment, a surgical instrument according to the disclosure comprises an instrument shaft, a tool at a distal shaft end and a handle at a proximal shaft end, the handle comprising a steering gear with at least two drives for the alignment of a wobble plate. This wobble plate is rotatively coupled to a main shaft which is rotatable about a main axis A and gimbal-mounted about a center Z located on the main axis A. Further, the wobble plate is connected to a plurality of steering wires which extend through the instrument shaft along the main axis A to an angling mechanism of the tool. The steering gear of the surgical instrument according to the disclosure is a steering gear according to the disclosure, in accordance with at least one of the above-described embodiments.

Further embodiments, and some of the advantages connected to these and further embodiments, are rendered clear and better understandable by the following detailed description which makes reference to the attached figures. Objects or parts thereof which are substantially the same or similar may be provided with the same reference signs. The figures are merely a schematic illustration of an embodiment of the disclosure. It will be appreciated that the features mentioned above and the features yet to be explained below are applicable not only in the respectively specified combination but also in other combinations or on their own, without departing from the scope of the present disclosure.

DETAILED DESCRIPTION OF PREFERRED EMBODIMENTS

Figure 1:
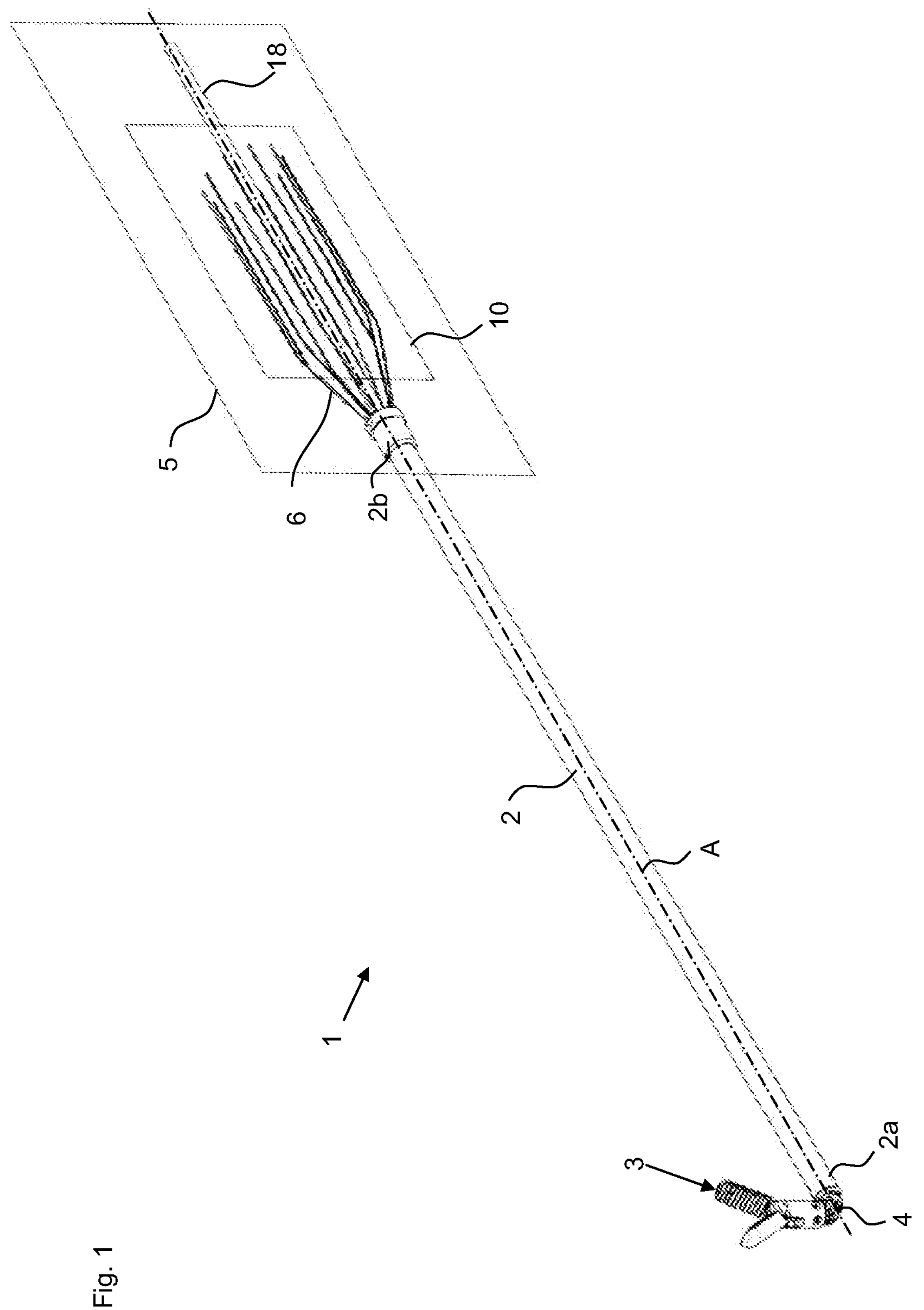
FIG. 1 shows a perspective partial view of a surgical instrument according to the disclosure with a schematically depicted handle.

FIG. 1 shows a surgical instrument 1 with a hollow instrument shaft 2, wherein a handle 5 arranged at the proximal end **2*b* of the instrument shaft 2 is only depicted schematically. A tool 3 is arranged at the distal end 2*a* of the instrument shaft 2 and can be, for example, a tool 3 provided with jaw parts, as depicted in FIG. 1, or else an endoscope, an applicator, or the like. To actuate the tool 3, for example for the purpose of opening and closing the jaw parts, the surgical instrument 1 comprises an actuation element 18 which is axially displaceably mounted in the instrument shaft 2 and operatively connected on the proximal side to an actuation unit (not depicted here) of the handle 5. The actuation unit can be a manually actuatable grip or a component designed for robotic use, which is to say a component that is actuatable without manual assistance as well, said component being coupled to a corresponding drive. The actuation element 18 which is axially displaceably mounted in the instrument shaft 2 and which serves to actuate the tool 3** is designed as a pull/push rod in the illustration.

Moreover, the tool 3 of the surgical instrument 1 is pivotable relative to the main axis A of the instrument shaft 2 by way of an angling mechanism 4 at the distal shaft end **2*a*. The angling mechanism 4 consists of pivot members which are connected to the steering gear 10 in the handle 5 at the proximal end 2*b* of the instrument shaft 2 by way of steering wires 6 which extend through the instrument shaft 2. A movement of the proximal-side steering gear 10 thus causes a corresponding relative movement, transmitted by the steering wires 6, of the distal-side pivot members of the angling mechanism 4, and hence causes pivoting of the tool 3. Even though use is made of the term steering wires 6 in the present case, from a functional point of view use can also be made of steering cables, which is why the used term steering wires 6** should also be read and understood synonymously as steering cables.

Figure 2:
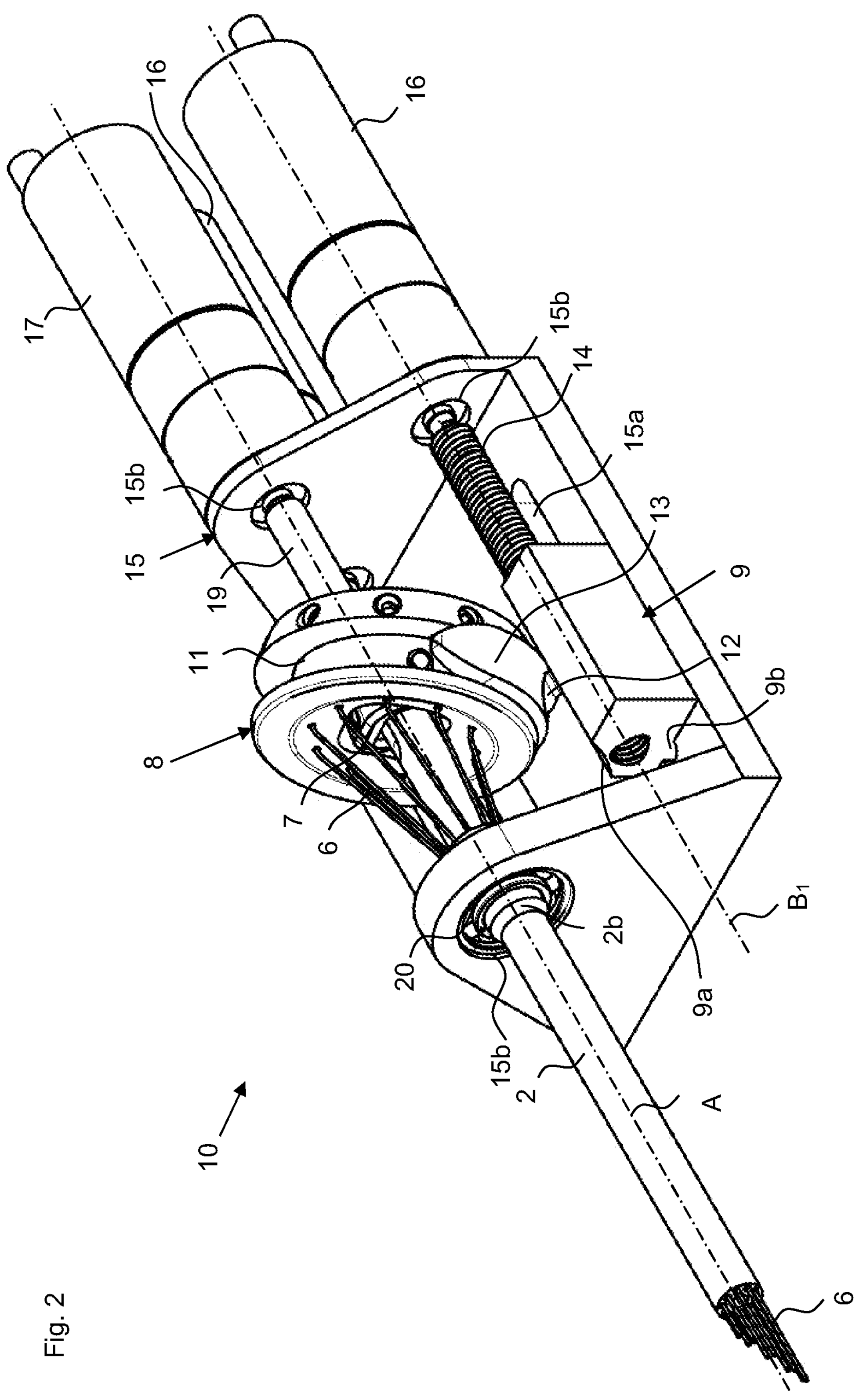
FIG. 2 shows a perspective view of a steering gear in accordance with a preferred embodiment according to the disclosure.
Figure 3:
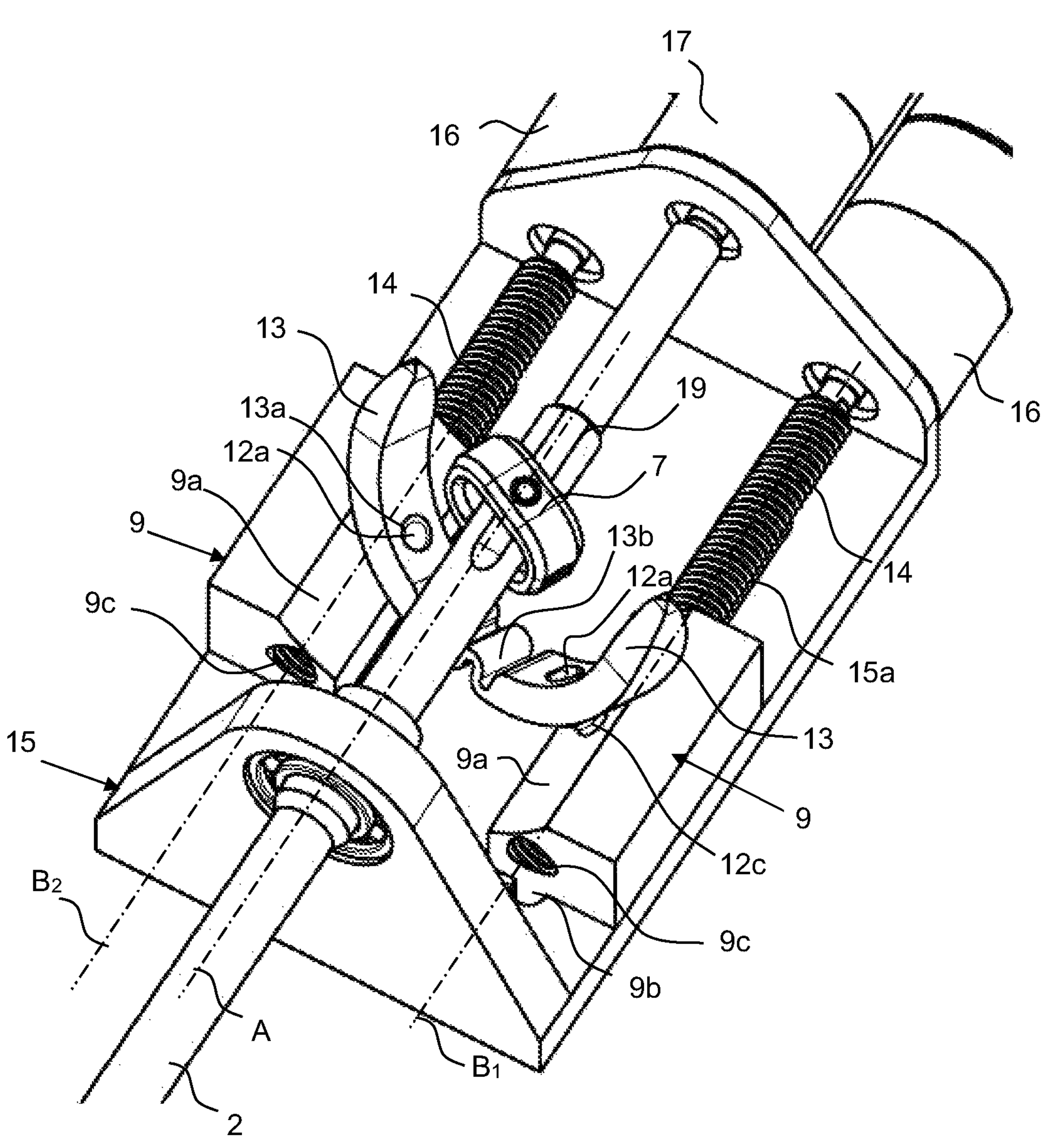
FIG. 3 shows a perspective partial view of the steering gear from FIG. 2 without the wobble disk being depicted.
Figure 4:
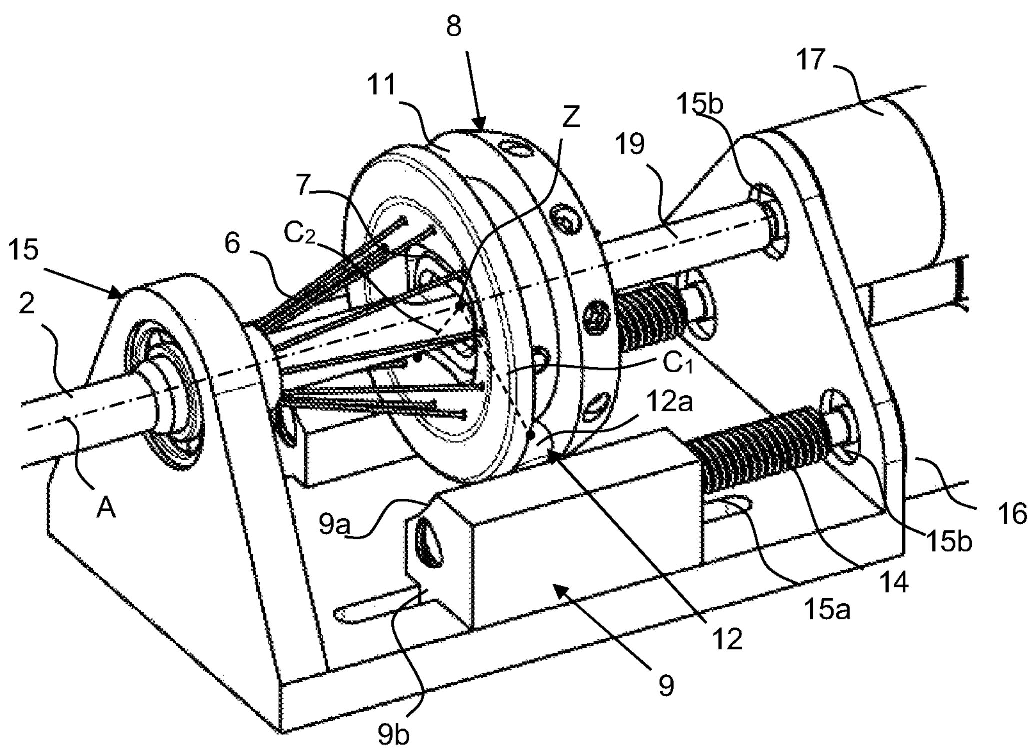
FIG. 4 shows a perspective view of a steering gear in accordance with a further embodiment according to the disclosure.

The steering gear 10, for which different examples are shown in FIGS. 2 to 8, comprises a wobble plate 8, fastened to which are the steering wires 6 which emerge from the proximal shaft end **2*b*, as is evident from FIGS. 2 and 4. In this case, the wobble plate 8 is coupled for rotation with a main shaft 19 which adjoins the proximal end 2*b* of the instrument shaft 2 along the main axis A. At its proximal end 2*b*, the instrument shaft 2 is rotatably mounted in a passage opening 15*b* in the housing component 15 of the steering gear 10 by means of bearings 20. On the proximal side, the main shaft 19 extends through a further passage opening 15*b* in the housing component 15 and is operatively connected to a rotary drive 17. As a result of the rotative coupling of the main shaft 19 with the wobble plate 8, the tool 3 at the distal shaft end 2*a* can also be rotated about the main axis A of the instrument shaft 2 without the steering wires 6** becoming twisted.

For the purpose of pivoting about two spatial axes orthogonal to the main axis A, the wobble plate 8 is gimbal-mounted about a center Z located on the main axis A. In the case of a conventional gimbal mount with two orthogonal axis pairs, the center Z is located at the point of intersection of the two axis pairs and may correspond to the wobble plate center or wobble plate centroid.

To spatially pivot the gimbal-mounted wobble plate 8 about its center Z, the steering gear 10, depending on exemplary embodiment, comprises two linear slides 9 (FIGS. 2 to 6) or three or four linear slides 9 (FIGS. 7, 8) which are operatively connected to the wobble plate 8. In this case, the linear slides 9 are connected to drives 16 such that the steering wires 6 for pivoting the distal-side pivot members of the angling mechanism 4 or tool 3 can be controlled precisely, delicately with very small increments, and also reproducibly.

In the example shown in FIGS. 2 to 4, the wobble plate 8 comprises a central passage opening (without reference sign) which is concentric with the main axis A and in which a universal joint plate 7 is arranged, the latter in turn comprising a passage opening (without reference sign), through which the main shaft 19 extends. The universal joint plate 7 is pivotably connected to the wobble plate 8 by way of a first axis pair. The universal joint plate 7 is pivotably connected to the main shaft 19 by way of a second axis pair, which is arranged orthogonal to the first axis pair: this can be seen easily in the illustration of FIG. 3 without the wobble plate. In this case, the point of intersection of the two axis pairs, which defines the center Z of the wobble plate, is located in the center of the passage opening of the universal joint plate 7, which also corresponds to the center of the passage opening of the wobble plate 8. In this case, the gimbal mount with the universal joint plate 7 by way of the two axis pairs also ensures the rotative coupling of the wobble plate 8 to the main shaft 19.

Not depicted here are alternative embodiments of the gimbal mount of the wobble plate, which for example may also be in the form of an outside gimbal mount with an outer clamp (rather than a closed ring), which has a cutout in the region of the linear slides and which is connected to an inner ring by way of a first axis pair. Said inner ring is connected to a circumferential portion of the wobble plate by way of a second axis pair orthogonal to the first axis pair. Then, a central wobble plate portion, to which the steering wires are fastened and which is coupled for rotation with the main shaft, is rotatably mounted in the circumferential portion of the wobble plate.

The steering gear 10 of the examples in FIGS. 2 to 6 comprises two linear slides 9, which are arranged parallel to the rotary drive 17 of the main shaft 19. As a result of the connection to a drive 16, each linear slide 9 can be displaced independently along a guide axis $B_1$. $B_2$ that is parallel to the main axis A. The drives 16 used to actuate the linear slides 9 can also be rotary motors 16, as depicted in FIGS. 2 and 3. To this end, the rotary motors 16 are connected to the respective linear slide 9 via a respective spindle 14, the linear slide to this end comprising a drilled spindle hole 9*c* along the respective guide axis $B_1$, $B_2$. As an alternative to a rotary motor with spindle, a linear motor or a hydraulic or pneumatic cylinder, for example, can be used as drive 16.

To transmit the movement of the respective linear slide 9 to the wobble plate 8, in order to pivot the latter about its center Z, each linear slide 9 is operatively connected to the wobble plate 8 by way of an engagement element pair. As described below, the engagement elements of an engagement element pair may have different designs. However, as one of the engagement elements, each engagement element pair comprises a lever element 12 with a head portion 12*a*, 12*b*, which is movably accommodated in an engagement opening 11, 11*a*, 11*b*, 11*c* that represents the other engagement element. In this case, one of the engagement elements of the engagement element pair is present on a circumference of the wobble plate 8 and the other engagement element of the engagement element pair is located on a surface portion 9*a* of the respective linear slide 9, which faces the wobble plate 8. In this way, the head portions 12*a*, 12*b* of the lever elements 12 are always located on a circumferential line around the center Z of the wobble plate 8.

The surface portion 9*a*, which faces the wobble plate 8 and on which the respective engagement element is present, is formed as a concave surface portion 9*a* on a longitudinal side of the linear slide 9 parallel to the guide axis $B_1$, $B_2$. In this case, the surface portion 9*a* corresponds to a lateral cylindrical surface portion around the main axis A with a radius slightly greater than the radius of the wobble plate 8. In this case, the pivot plane of the wobble plate 8 is defined by the center Z of the gimbal mount and the engagement points of the head portions 12*a*, 12*b* on the free end of the rod portions 12*c* of the lever elements 12.

For the axially parallel guidance of the linear slides 9, a respective guide groove 15*a*, in which a guide element 9*b* of the respective linear slide 9 is displaceably accommodated, is formed parallel to each guide axis $B_1$, $B_2$ in the housing component 15. The guide element 9*b* is in the form of an elongate tread element which is located on the underside of the linear slide 9 and which extends parallel to the guide axis $B_1$, $B_2$ in the longitudinal direction. In a design of the housing component and the linear slide that deviates from the exemplary representation, it is alternatively possible for the guide element on the linear slide to be present not on its underside but on another adjacent side face, which does not have the surface portion 9*a* facing the wobble plate 8.

Further, the arrangement of guide element and guide groove on linear slide and housing component may also be reversed in an embodiment not depicted here, which is to say the linear slide comprises a longitudinal groove and an elongate guide element, on which the linear slide with the longitudinal groove is displaceable, is present on the housing component. Deviating from the combination of guide element and guide groove, the linear guide of the linear slide of a steering gear according to the disclosure may also comprise other, known linear guide elements, for example C-profiles or shafts.

Figure 5:
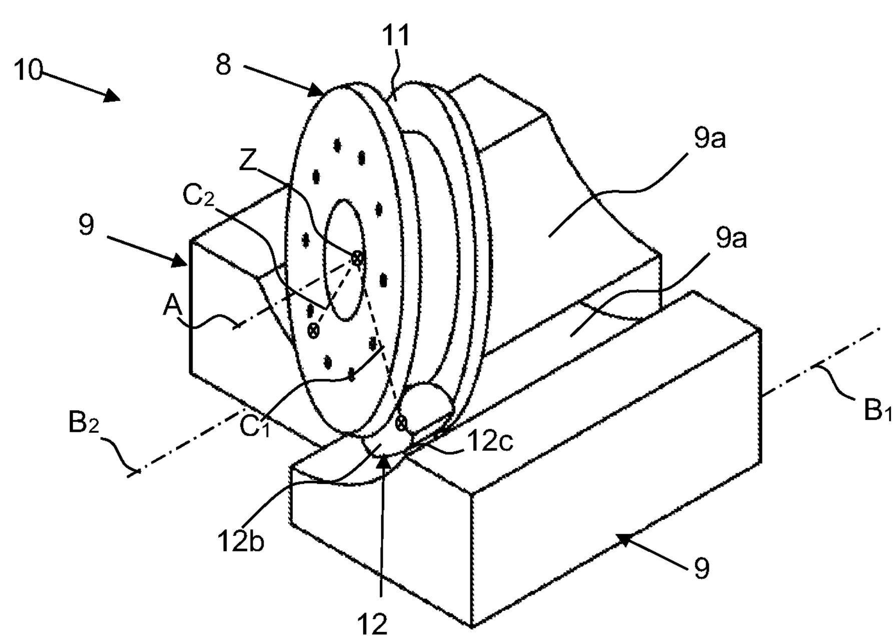
FIG. 5 shows a perspective view of wobble plate and linear slides of a steering gear in accordance with a further embodiment according to the disclosure.
Figure 6:
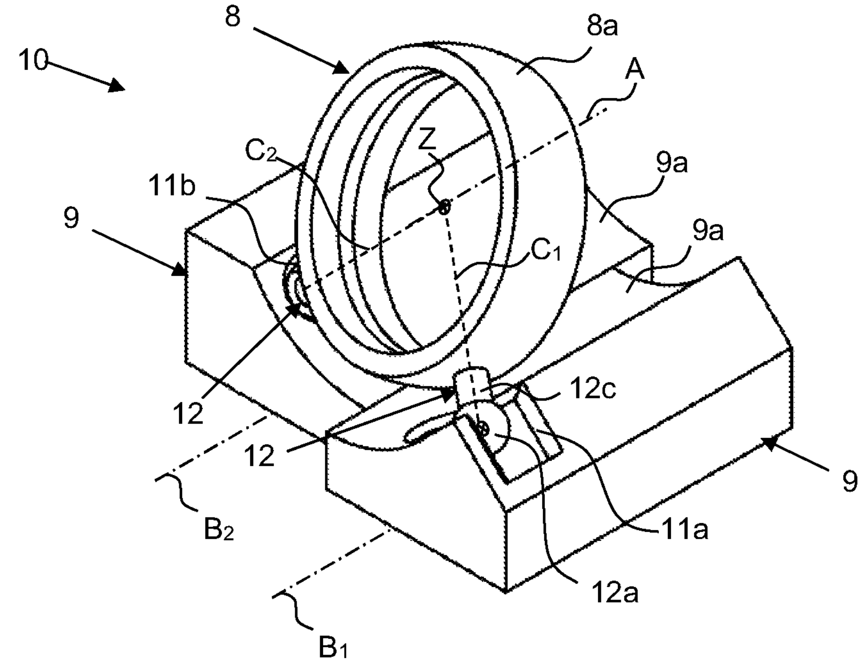
FIG. 6 shows a perspective view of wobble plate and linear slides of a steering gear in accordance with a further embodiment according to the disclosure.

Apart from the example in FIG. 6, the lever elements 12 are arranged on the linear slides 9 in the steering gears 10, while the associated engagement opening is formed in the wobble plate 8, to be precise in the form of a circumferential groove 11 (FIGS. 2, 4, 5) all around the circumferential edge of the wobble plate 8 or in the form of a circumferential recess 11*c* (FIGS. 7, 8) all along the circumferential edge of the wobble plate 8. In this case, the all-round circumferential groove 11 or all-round circumferential recess 11*c* forms a common engagement element for all lever elements 12. Each lever element 12 is arranged on the concave surface portion 9*a* of the respective linear slide 9, with the result that the rod portion 12*c* points in the radial direction toward the main axis A and hence the head portion 12*a*, 12*b* can be accommodated in the circumferential groove 11 or can come to rest against the circumferential recess 11*c*.

As a result of the guidance in the circumferential groove 11 or on the circumferential recess 11*c*, the centers of the head portions 12*a*, 12*b* are thus located on a circumferential line around the wobble plate center Z and hence always exactly in the pivot plane of the wobble plate 8. If the linear slides 9, and hence the lever elements 12, are moved parallel to the main axis A along the respective guide axis $B_1$, $B_2$, these centers of the head portions 12*a*, 12*b* are displaced accordingly and thus lead to the pivoting of the wobble plate 8. Since the circumferential groove 11 or circumferential recess 11*c* is all around, the wobble plate 8 can nevertheless be freely rotated with the main shaft 19. Thus, the wobble plate 8 firstly can be pivoted in two directions vis-à-vis the main axis A and the fastened steering wires 6 can be deflected to different extents and secondly can be rotated together with the main shaft 19 such that the tool 3 of the surgical instrument 1 from FIG. 1 can be accordingly angled at the distal end 2*a* of the instrument shaft 2 and/or rotated about the main axis A.

FIG. 4 shows the wobble plate 8 in a neutral position in which the main axis A runs orthogonal to the pivot plane defined by the center Z of the wobble plate 8 and the spherical head portions 12*a*, which are accommodated in the circumferential groove 11 of the wobble plate 8 and guided on both sides. In this case, the arrangement of the two linear slides 9 in relation to the wobble plate 8 and the arrangement of the lever elements 12 on the two linear slides 9 are matched to one another in such a way in the example shown that two pivot axes $C_1$, $C_2$, which are defined by the two spherical head portions 12*a* of the two lever elements 12 together with the center Z of the wobble plate 8, run orthogonal to one another in the neutral position of the wobble plate 8. The spherical head portion 12*a* has an approximately spherical shape, although it may be flattened on the side pointing to the wobble plate 8, as evident from the examples in FIGS. 3, 7 and 8.

The position of the pivot plane of the wobble plate 8, which is defined by the two pivot axes $C_1$, $C_2$, is determined by the position of the linear slides 9, wherein the pivoting of the wobble plate 8 in relation to the main axis A is rendered possible by the gimbal mount. The wobble plate 8 is pivoted out of the neutral position by displacing one or both linear slides 9 along the respective guide axis $B_1$, $B_2$; for example, this can be seen in FIG. 2 or 5, these figures showing exemplary embodiments similar to that in FIG. 4. The steering gear 10 in FIG. 2 differs from FIG. 4 in the arrangement of two slide block elements 13, which improve the force transmission from the lever elements 12 to the wobble plate 8 by virtue of increasing the contact area vis-à-vis the spherical head portion 12*a*. The slide block elements 13 are designed for guidable accommodation in the circumferential groove 11 and comprise a ball socket 13*a* for movable accommodation of the spherical head portion 12*a* (cf. the representation without wobble plate in FIG. 3). The slide block elements 13 transmit the steering forces of the spherical head portions 12*a* accommodated in the ball sockets 13*a* to the wobble plate 8 over an area as a result of the arrangement in the circumferential groove 11. Since the spacing of the two spherical head portions 12*a* varies when the linear slides 9 are actuated, the two slide block elements 13 are interconnected by way of a flexible connection piece 13*b* in the example shown, in order to form a type of clamping element. Alternatively, the slide block elements 13 can be embodied independently of one another as individual slide blocks 13.

The difference between the steering gears 10 in FIGS. 4 and 5 consists of the lever elements 12 in FIG. 5 being formed with a T-head portion 12*b* instead of a spherical head portion 12*a* like in FIG. 4. The T-head portion 12*b* has a cylinder-like shape similar to a torus section, which is to say, as it were, a cylinder bent along the cylinder axis, the bending radius thereof corresponding to the circumference of the wobble plate 8 in the circumferential groove 11. In this case, the cross section of the T-head portion 12*b* has a circular segment shape leading to a flattened side of the lateral surface on which the T-head portion 12*b* is arranged on the rod portion 12*c* and which points to the concave surface portion 9*a* of the linear slide 9. With the rounded lateral surface, the T-head portion 12*b* is therefore in contact with the wobble plate 8 along a line in the circumferential groove 11. So that the T-head portions 12*b* can align themselves in the circumferential groove 11 when the wobble plate 8 is pivoted by the respective other linear slide 9, the lever elements 12, which comprise the T-head portion 12*b*, are mounted in the linear slide 9 so as be rotatable about the longitudinal axis of the rod portion 12*c*.

Figure 7:
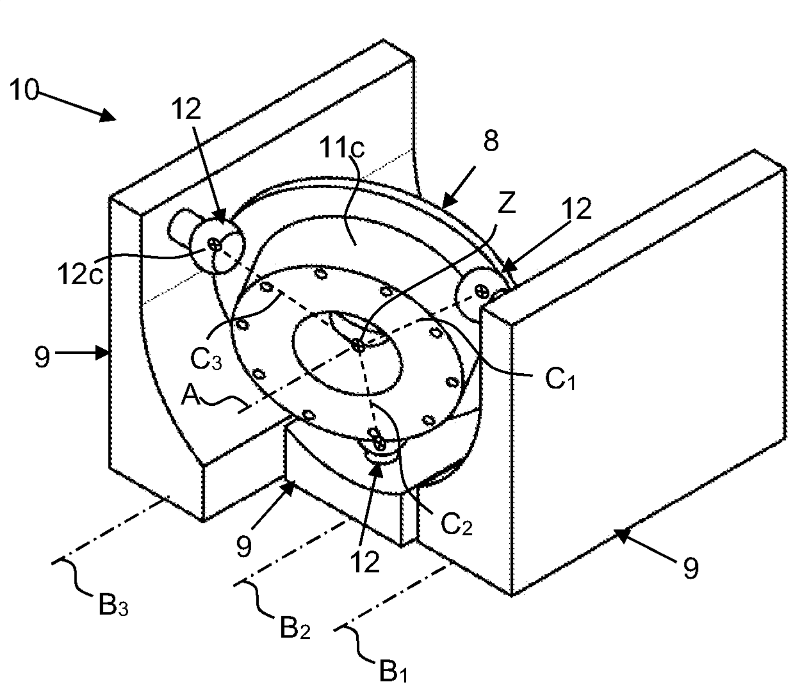
FIG. 7 shows a perspective view of wobble plate and linear slides of a steering gear in accordance with a further embodiment according to the disclosure.
Figure 8:
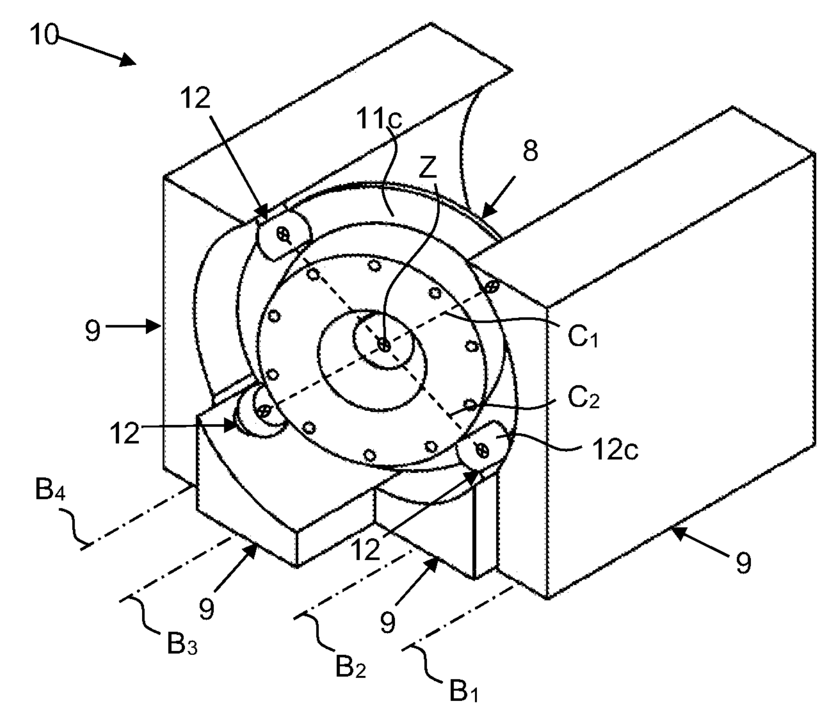
FIG. 8 shows a perspective view of wobble plate and linear slides of a steering gear in accordance with a further embodiment according to the disclosure.

The alternative embodiments of the steering gears 10 in FIGS. 7 and 8 use a circumferential recess 11*c* as engagement opening on the wobble plate 8, said circumferential recess providing a contact to the spherical head portion 12*a* of the lever element 12 that acts only on one side. Therefore, three linear slides 9 with three lever elements 12 (FIG. 7) or four linear slides 9 with four lever elements 12 (FIG. 8) are required to define all spatial positions of the wobble plate 8. Like a ring flange, the circumferential recess 11*c* has a distal-side cylinder portion and, offset therefrom, a proximal-side disk portion with an increased diameter. Thus, the spherical head portions 12*a* of the lever elements 12 rest against the disk portion of the circumferential recess 11*c* on the distal side. To ensure the engagement of the lever elements 12 on the circumferential recess 11*c* delimited on one side in this way, the steering wires 6, which are fastened to the end face of the distal-side cylinder portion, can be tensioned in a defined manner during operation by a tensioning mechanism. As a result, the center Z of the wobble plate 8 can be displaced linearly along the main axis A, with the result that the wobble plate 8 is pulled in the distal direction by means of the steering wires 6 so that the circumferential recess 11*c* rests against the head portions 12*a*.

In the variant of FIG. 7 with three linear slides 9, provision is made of three drives (not depicted here) which are connected to the linear slides 9 in order to be able to move each linear slide 9 independently along the three guide axes $B_1$, $B_2$, $B_3$ for the purpose of aligning the wobble plate 8. The arrangement of the lever elements 12 on the respective linear slides 9 and the arrangement of the three linear slides 9 in relation to the wobble plate 8 are in this case matched to one another in such a way that the three head portions 12*a* define three pivot axes $C_1$, $C_2$, $C_3$, which each have an angle of 120° from one another, together with the center Z of the wobble plate. In this case, the center Z of the wobble plate 8 arises as the center of the circular line on which the three head portions 12*a* are arranged uniformly spaced apart from one another. Since the position of the wobble plate 8 in relation to two spatial directions orthogonal to the main axis A is uniquely determined by the three head portions 12*a* and hence the gimbal mount is provided within the meaning of the disclosure, it is possible to dispense with gimbal mount elements such as the universal joint plate 7 with the two orthogonal axis pairs from the example in FIGS. 2 to 4. However, an alternative mounting concept is then required for the rotative coupling of the wobble plate 8 with the main shaft 19 (not depicted in FIG. 7), said mounting concept permitting the transfer of rotary angles of the main shaft to the wobble plate 8 without impeding the pivoting of the wobble plate 8 vis-à-vis the main axis A.

According to such an alternative mounting concept, provision is made for the wobble plate to comprise a radially inwardly pointing pin or a diametrically inwardly pointing pin pair in its passage opening and for a guide groove or two diametric guide grooves to be formed accordingly in the main shaft, said guide groove(s) extending in the longitudinal direction of the main shaft. The engagement of the pin(s) in the guide groove(s) brings about the rotative coupling of the main shaft with the wobble plate and at the same time permits a pivoting of the wobble plate in two orthogonal spatial directions: a pivoting about the axis of the pin/pair of pins, since each pin can rotate about its axis in the respective guide groove, and a tilting of the pin in a plane spanned thereby together with the guide groove, corresponding to a pivoting of the wobble plate about an axis running orthogonal to the pin axis and the main axis A.

In order to be able to dispense with a third drive for aligning the wobble plate 8, four linear slides 9 with four lever elements 9 are used in the example of FIG. 8. Accordingly, this steering gear 10 provides for four guide axes $B_1$, $B_2$, $B_3$, $B_4$, along which the four linear slides 9) can move for the purpose of aligning the wobble plate 8. In this case, the arrangement of the lever elements 12 on the four linear slides 9 and the arrangement of the four linear slides 9 in relation to the wobble plate 8 are matched to one another in such a way that the head portions 12*a* are arranged spaced uniformly apart from one another on a circular line around the center Z of the wobble plate 8, with the result that two respective head portions 12*a* are arranged diametrically opposite one another. Accordingly, the two head portions 12*a* of opposing lever elements 12 each define a pivot axis $C_1$, $C_2$, said pivot axes running orthogonal to one another in the neutral position of the wobble plate 8 and intersecting at the center Z of the wobble plate 8. In this case, the linear slides 9 of opposing lever elements 12 are not controlled independently of one another, but precisely in the opposite sense, as is evident in FIG. 8 from the position of the linear slides 9 along the guide axes $B_1$, $B_2$, $B_3$, $B_4$. The linear slide 9) (whose lever element is covered in the illustration) guided along the first guide axis $B_1$ is offset in the proximal direction, corresponding to the offset in the distal direction of the linear slide 9 guided along the third guide axis $B_3$. A corresponding statement applies to the linear slides 9 guided along the guide axes $B_2$ and $B_4$. The opposite control of the linear slides 9 of opposing lever elements 12 can be realized by a reversing gear not depicted here (e.g., using a contra-rotating spindle, etc.), with the result that the linear slides 9 of opposing lever elements 12 can be moved by the same drive in each case, and hence only two drives are required for four linear slides.

In the example of an alternative steering gear 10 depicted in FIG. 6, the lever elements 12 are arranged on the wobble plate 8. The corresponding engagement openings 11*a*, 11*b* for the head portions 12*a* are present in the linear slides 9. In this case, an arcuate groove 11*a*, which runs around the main axis A and in which the spherical head portion 12*a* of one of the lever elements 12 is guidably accommodated, is formed in the concave surface portion 9*a* in a linear slide 9 guided along the first guide axis $B_1$. The other linear slide 9, which is guided along the second guide axis $B_2$, comprises in the concave surface portion 9*a* a cylindrical drilled hole 11*b* whose axis intersects the main axis A at right angles and which movably accommodates the spherical head portion 12*a* of the second lever element 12. Since the lever elements 12 would prevent a rotation of the wobble plate 8 about the main axis A in this arrangement, the wobble plate 8 in this embodiment is divided into a circumferential portion 8*a*, on which the lever elements 12 are arranged, and a central portion not depicted here. This central portion is rotatably mounted in the circumferential portion 8*a* and provided for fastening the steering wires. The gimbal mount of the central portion on the main shaft and its rotative coupling can be implemented by means of a universal joint plate and two crossed axis pairs as described above, which determine the center Z of the wobble plate 8. The pivot axes $C_1$, $C_2$, which are defined by the spherical head portions 12*a* of the lever elements 12 together with the center Z of the wobble plate 8, run orthogonal to one another. In this case, the lever elements 12 accordingly extend with a 90° offset in the radial direction, from the circumferential edge of the circumferential portion 8*a* of the wobble plate 8.

The drawings, the description, and the claims contain numerous features in combination. It will be appreciated that the aforementioned features are applicable not only in the respectively specified combination but also in other combinations or on their own, without departing from the scope of the present disclosure. The present disclosure provides a steering gear 10 for a surgical instrument 1 and the surgical instrument 1 itself, the steering gear 10 comprising at least two drives 16 for the spatial alignment of a wobble plate 8. The wobble plate 8 is rotatively coupled to a main shaft 19 which is rotatable about a main axis A and gimbal-mounted about a center Z located on the main axis A. The steering gear 10 comprises at least two linear slides 9, which are each displaceably arranged along a guide axis $B_x$ parallel to the main axis A and connected to the at least two drives 16. Each linear slide 9 is operatively connected to the wobble plate 8 by way of an engagement element pair having, as engagement elements, an engagement opening 11, 11*a*, 11*b*, 11*c* and a lever element 12 comprising, at a free end of a rod portion 12*c*, a head portion 12*a*, 12*b* for movable accommodation in the engagement opening 11, 11*a*, 11*b*, with a pivot plane of the wobble plate 8 being defined by the head portions 12*a*, 12*b* of the lever elements 12 and the center Z of the wobble plate 8. In this case, one of the engagement elements of the engagement element pair is present on a circumference of the wobble plate 8 and the other engagement element of the engagement element pair is present on a surface portion 9*a* of the respective linear slide 9 facing the wobble plate 8, said surface portion being a surface portion 9*a* on a longitudinal side of the linear slide 9 parallel to the guide axis $B_x$.

The invention claimed is:

1. A steering gear for a surgical instrument, the steering gear comprising:
   - at least two drives for a spatial alignment of a wobble plate, the wobble plate being rotatively coupled to a main shaft which is rotatable about a main axis and gimbal-mounted about a center located on the main axis; and
   - at least two linear slides, which are each displaceably arranged along a guide axis parallel to the main axis and connected to the at least two drives, with each linear slide being operatively connected to the wobble plate by way of an engagement element pair having, as engagement elements, an engagement opening and a lever element comprising, at a free end of a rod portion, a head portion for movable accommodation in the engagement opening, with a pivot plane of the wobble plate being defined by the head portions of the lever elements and the center of the wobble plate, and
   - with one of the engagement elements of the engagement element pair being present on a circumference of the wobble plate and the other engagement element of the engagement element pair being present on a surface portion of the respective linear slide facing the wobble plate, said surface portion being a surface portion on a longitudinal side of the linear slide parallel to the guide axis.

2. The steering gear as set forth in claim 1, wherein the head portion is a spherical head portion having a spherical shape at least in part or a T-head portion shaped cylindrically at least in part.

3. The steering gear as set forth in claim 2, wherein at least two of the lever elements, which extend from a circumferential edge of the wobble plate in a radial direction and are formed with the spherical head portion, are arranged on the wobble plate, and of the at least two linear slides, a first linear slide comprises, as engagement opening, an arcuate groove running around the main axis and a second linear slide comprises, as engagement opening, a cylindrical drilled hole, said engagement openings being formed in the surface portion of the respective linear slide facing the wobble plate, the spherical head portion of a first of the lever elements being movably accommodated in the arcuate groove in the first linear slide and the spherical head portion of a second of the lever elements being movably accommodated in the cylindrical drilled hole in the second linear slide, and the arrangement of the engagement openings in the linear slides and the arrangement of the at least two linear slides in relation to the wobble plate being matched to the arrangement of the at least two lever elements on the wobble plate, and the wobble plate having a central portion which is rotatively coupled to the main shaft and rotatably mounted in a steering ring of the wobble plate, said steering ring having the circumferential edge on which the at least two lever elements are arranged.

4. The steering gear as set forth in claim 1, wherein the wobble plate comprises the engagement opening and each linear slide comprises a respective one of the lever elements, the engagement opening being a circumferential groove running all along a circumferential edge of the wobble plate or a circumferential recess running all along the circumferential edge of the wobble plate, and the lever element being arranged on the surface portion of the respective linear slide facing the wobble plate such that the rod portion points to the main axis in a radial direction, and the head portion of each lever element being movably accommodated in the circumferential groove or in the circumferential recess.

5. The steering gear as set forth in claim 4, wherein the engagement element pair further comprises a slide block element for each lever element with the head portion, said slide block element being designed to be accommodated in the circumferential groove or in the circumferential recess and comprising a ball socket designed for movable accommodation of the head portion.

6. The steering gear as set forth in claim 4, wherein the wobble plate is designed with the circumferential groove as engagement opening and the steering gear comprises two linear slides, with the arrangement of the lever elements on the two linear slides and the arrangement of the two linear slides in relation to the wobble plate being matched to one another in such a way that two differently oriented pivot axes are defined by the head portion of each of the two lever elements together with the center of the wobble plate, with the two pivot axes running orthogonal to one another.

7. The steering gear as set forth in claim 4, wherein the wobble plate is designed with the circumferential recess as engagement opening and the steering gear comprises three linear slides connected to three drives, with the arrangement of the lever elements on the three linear slides and the arrangement of the three linear slides in relation to the wobble plate being matched to one another in such a way that three differently oriented pivot axes are defined by the three head portions the three lever elements together with the center of the wobble plate, with the three pivot axes each having an angle of 120°±10° with respect to one another.

8. The steering gear as set forth in claim 4, wherein the wobble plate is designed with the circumferential recess as engagement opening and the steering gear comprises four linear slides, with the arrangement of the lever elements on the four linear slides and the arrangement of the four linear slides in relation to the wobble plate being matched to one another in such a way that two pivot axes, which are defined by two of the head portions, the lever elements of which are arranged opposite one another, together with the center of the wobble plate in each case, run orthogonal to one another, the linear slides of opposing lever elements being connected in pairwise fashion to the two drives.

9. The steering gear as set forth in claim 1, wherein the steering gear comprises at least one housing component which provides a linear guide for each linear slide, and/or the surface portion is a concave surface portion which corresponds to a lateral cylindrical surface portion around the main axis.

10. The steering gear as set forth in claim 1, wherein the drive, to which the linear slide is connected, is a linear motor, a rotary motor connected to the linear slide via a spindle, or a hydraulic or pneumatic cylinder.

11. A surgical instrument comprising an instrument shaft, a tool at a distal shaft end and a handle at a proximal shaft end, the handle comprising a steering gear with at least two drives for the alignment of a wobble plate which is rotatively coupled to a main shaft which is rotatable about a main axis, and the wobble plate being gimbal-mounted about a center located on the main axis and connected to a plurality of steering wires which extend through the instrument shaft along the main axis to an angling mechanism of the tool, wherein the steering gear is the steering gear as set forth in claim 1.

* * * * *